United States Patent [19]

Baumann et al.

[11] Patent Number: 4,788,209

[45] Date of Patent: Nov. 29, 1988

[54] ANTIFUNGAL 2-ANILINOTHIAZOLINES

[75] Inventors: Russell J. Baumann; Boyd L. Harrison, both of Cincinnati, Ohio

[73] Assignee: Merrell Dow Pharmaceuticals Inc., Cincinnati, Ohio

[21] Appl. No.: 15,246

[22] Filed: Feb. 17, 1987

[51] Int. Cl.$^4$ .................. C07D 277/42; A61K 31/425
[52] U.S. Cl. ..................................... 514/370; 548/190
[58] Field of Search ................... 548/190; 514/370

[56] References Cited

U.S. PATENT DOCUMENTS

| | | | |
|---|---|---|---|
| 2,027,030 | 1/1936 | Engelmann | 548/190 |
| 3,164,605 | 1/1965 | Sovish | 548/190 |
| 3,636,219 | 1/1972 | Culik | 514/291 |
| 3,651,053 | 3/1972 | Sagner | 544/053 |
| 3,737,536 | 6/1973 | Sagner | 514/226 |
| 3,993,766 | 11/1976 | Behner | 514/370 |
| 4,145,421 | 3/1979 | Heumann | 514/249 |

FOREIGN PATENT DOCUMENTS

| | | |
|---|---|---|
| 1356908 | 4/1964 | France . |
| 18463 | 2/1975 | Japan . |
| 106674 | 7/1982 | Japan .................. 514/370 |
| 144205 | 9/1982 | Japan . |

OTHER PUBLICATIONS

M. Tisler. Synthesis and rearrangement of 1-substituted thiocarbamylethylenimines to N-substituted derivatives of 2-amino-2-thiazoline. Arch. Pharm. 291 457 (1958) CA53:6208i.

H. Najer, et al., 2-Aralkylamino- or arylaminothiazolines possessing vascular activity. Bull. Soc. Chim. France 1960, 960. CA55:1582e.

R. Zhao, et al., Preparation and application of "Jing Song Ling": - a veterinary sedative, analgesic and myorelaxant.

Zhongguo Nongye (Beijing) Kexue (4) 9 (1981). CA96:115796p.

Primary Examiner—Robert Gerstl
Attorney, Agent, or Firm—Edlyn S. Simmons

[57] ABSTRACT

Fungal infections of the skin and mucous membranes may be controlled by topical administration of a pharmaceutical composition comprising a N-(3- or 4-alkylphenyl)4,5-dihydro-2-thiazolamine.

15 Claims, No Drawings

ANTIFUNGAL 2-ANILINOTHIAZOLINES

This invention relates to novel 2-anilinothiazoline derivatives of formula I

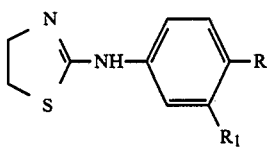

wherein (a) R is a straight chain alkyl group having from 4 to 8 carbon atoms and $R_1$ is hydrogen or (b) R is hydrogen and $R_1$ is a straight chain alkyl group having from 5 to 8 carbon atoms, and to the use of these compounds in pharmaceutical compositions for the treatment of fungal infections 2-Anilinothiazolines substituted on the phenyl ring by groups other than medium length alkyl chains are known from, for example, U.S. Pat. Nos. 2,027,030, 3,164,605, 3,737,536, and 3,993,766, and Japanese kokai Nos. 57-106674 and 57-144205. The prior art compounds have been reported to have activity as central nervous system depressants, muscle relaxants, acaricides and herbicides.

It has now been discovered that 2-anilino-2-thiazolines wherein the phenyl moiety is substituted in the 4-position by a linear alkyl chain having from 4 to 8 carbon atoms or in the 3-position by a linear alkyl chain having from 5 to 8 carbon atoms demonstrate pronounced antimycotic activity, rendering them suitable for the treatment of fungal infections of the skin and mucous membranes.

The 2-anilinothiazolines of this invention exist in the form of tautomers whose structure may be illustrated in two forms. Structure Ia, which is a N-(substituted

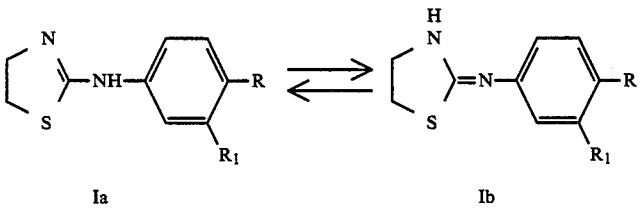

Ia  Ib phenyl)-4,5-dihydro-2-thiazolamine, and structure Ib, which is a N-substituted phenyl)-2-thiazolidinimine, exist at equilibrium at ordinary temperatures and pressures.

Pathogenic fungi are responsible for many of the diseases of the skin and mucous membranes of humans and other mammalian species. Dermatomycoses are among the most common cutaneous disorders, including such common diseases as atheletes foot (tinea pedis), jock itch (tinea cruris) and ringworm of the scalp (tinea capitis), which are commonly caused by fungi of the genera Trichophyton, Microsporum and Epidermophyton. Yeastlike imperfect fungi of the family Cryptococcaceae, order Moniliales, are responsible for some of the most prevalent of the dermatomycoses. The infective organisms, including fungi of the genera Candida and Torulopsis, are commonly present in the flora of the skin, mucous membranes and intestinal tract. Infections of the skin commonly occur in areas subject to moisture or intertrigo, for example, the folds of the groin or the corners of the mouth. Infections of the mucous membranes, commonly including thrush, pruritus ani and vaginal candidiasis, are frequently precipitated by the reduced resistance resulting from systemic illnesses and by disturbances of the normal flora resulting from pregnancy or treatment with drugs such as antibiotics and steroids.

Compounds of formula I are active as antifungal agents when applied topically to fungal infections of the skin and mucous membranes. Preferred compounds of formula I for the treatment of dermatomycoses are those wherein R is an alkyl chain of from 6 to 8 carbon atoms and $R_1$ is hydrogen. Most preferred is the compound of formula I wherein R is n-hexyl and $R_1$ is hydrogen.

The compounds of formula I are employed in the treatment of fungal infections in the form of pharmaceutical compositions wherein a compound of formula I is administered in combination with a carrier suitable for topical administration. Such compositions may be in the form of liquids such as solutions, emulsions and lotions, semi-solids such as ointments and creams, and solids, such as suppositories tablets and powders. Suitable vehicles for such compositions are well known in the art. The liquid compositions of this invention may be administered by direct application to the skin or as aerosol sprays, gargles or douches. Solid compositions may be applied to the skin or mucous membranes in the form of dusting powders and tablets or suppositories which may be administered intravaginally. Semisolid creams and ointments containing a compound of formula I may be applied to lesions on the surface of the skin or supplied intravaginally with an applicator of a type known to the art. Compositions of this invention may also incorporate a compound of formula I in a natural or synthetic polymeric matrix for sustained release in the form, for example, of a tampon or buccal patch. The compositions of this invention can be formulated in any convenient pharmaceutical vehicle, the compound of formula I being present in a wide range of concentrations, usually between 1% and 15% by weight of the composition. The concentration of the active compound will vary with the composition of the vehicle. Preferred compositions of this invention will contain from about 2 to about 6% by weight of a compound of formula I in a cream or ointment suitable for intravaginal administration.

The compounds of the present invention show activity against pathogenic fungi in vitro and in vivo. The activity of N-(4-hexylphenyl)-4,5-dihydro-2-thiazolamine against various yeast fungi commonly responsible for diseases of humans and animals is illustrated in Table I.

The compound was prepared in 20 ml aliquots of Mycophil agar at concentrations of 1.5 $\mu$M to 250 $\mu$M. The agar surfaces were innoculated with approximately $1 \times 10^5$ yeast cells/ml using a Steers-Foltz apparatus. The plates were incubated for 24 hours at 37° C. and examined for yeast growth. The minimal inhibitory concentration (MIC) is reported as the lowest concentration of compound that inhibited growth.

TABLE I

ACTIVITY AGAINST YEASTS OF
N—(4-HEXYLPHENYL)-4,5-DIHYDRO-2-THIAZOLAMINE

| Organism | MIC (µg/ml) |
|---|---|
| Candida albicans 1[a] | 8 |
| Candida albicans 8 | 8 |
| Candida albicans 10 | 8 |
| Candida albicans 14 | 8 |
| Candida albicans 16 | 8 |
| Candida tropicalis 4 | 8 |
| Candida tropicalis 20 | 8 |
| Candida pseudotropicalis | 2 |
| Candida parapsilosis | 4 |
| Torulopsis glabrata | 8 |

[a]Strain Number

To compare the activity of N-(4-hexylphenyl)-4,5-dihydro-2-thiazolamine with that of the well established antifungal agents miconazole and Clotrimazole, vaginal candidiasis was induced in rats.

Groups of 6 female, ovariectomized rats, 180–200 gram weight, were pretreated for 2 successive days with 0.5 mg of progesterone and 0.5 mg of estradiol administered subcutaneously to induce oestrus. Forty-eight hours later rats were infected intravaginally on 2 successive days with Candida albicans cells. Challenge levels of $1 \times 10^7$ and $1 \times 10^6$ cells were employed. Seventy-two hours after infection, the rats were treated topically (intravaginally) with 0.2 ml of a 10% solution of test compound in a vehicle consisting of the following: cetyl alcohol, 3.5 gm; glycerol monostearate polyethyleneglycol 100, 4.0 gm; diglycol stearate, 3.0 gm; polyethyleneglycol 400, 18.75 gm; and purified water, 18.75 gm.

Twenty-four hours after treatment, vaginal washings were collected, diluted and mixed with Mycosel agar in petri dishes. The dishes were incubated for 48 hours and colonies were counted to determine the surviving number of yeast cells per vaginal washing.

TABLE 2

SINGLE DOSE THERAPY OF RAT VAGINITIS INDUCED BY TWO CHALLENGE LEVELS

| Group | Challenge | Cells/ml Lavage | % Killed |
|---|---|---|---|
| N—(4-Hexylphenyl)-4,5-dihydro-2-thiazoleamine, 10% | $1 \times 10^7$ | $5 \times 10^3$ | 98 |
|  | $1 \times 10^6$ | $2 \times 10^3$ | 97 |
| Clotrimazole, 10% | $1 \times 10^7$ | $5 \times 10^4$ | 75 |

TABLE 2-continued

SINGLE DOSE THERAPY OF RAT VAGINITIS INDUCED BY TWO CHALLENGE LEVELS

| Group | Challenge | Cells/ml Lavage | % Killed |
|---|---|---|---|
|  | $1 \times 10^6$ | $1 \times 10^4$ | 83 |
| Miconazole, 10% | $1 \times 10^7$ | $2 \times 10^4$ | 90 |
|  | $1 \times 10^6$ | $7 \times 10^3$ | 88 |
| Control | $1 \times 10^7$ | $2 \times 10^5$ | — |
|  | $1 \times 10^6$ | $6 \times 10^4$ | — |

The compounds of this invention can be prepared by methods analogous to those previously described for the synthesis of prior art 2-anilinothiazolines, for example, the methods illustrated in U.S. Pat. Nos. 2,027,030, 3,164,605, and 3,993,766, and French Pat. No. 1,456,908. An illustrative reaction sequence is illustrated by the following Reaction Scheme A:

Reaction Scheme A

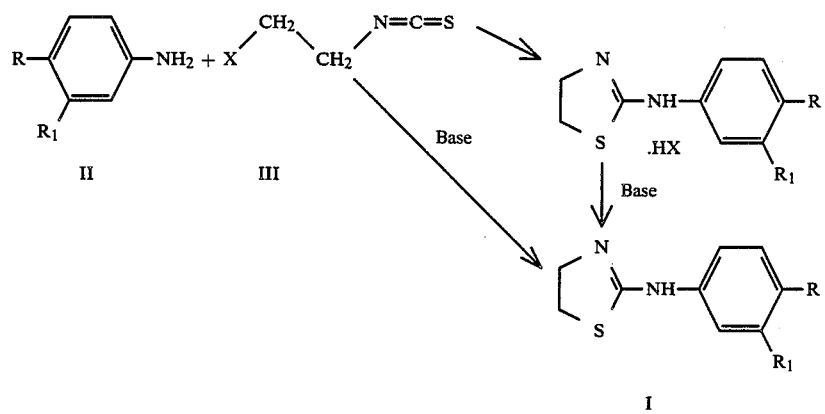

To a solution of a substituted aniline of formula II, wherein R and $R_1$ have the meanings defined above, is added a β-haloethylisothiocyanate of formula III, wherein X is a halogen atom, preferably chlorine, optionally dissolved in additional solvent, and the reaction mixture is stirred for from 1 to 72 hours at a temperature of from −30° C. to 100° C. Appropriate solvents include water, water soluble organic solvents including amides such as dimethylformamide, sulfoxides such as dimethylsulfoxide, ketones such as acetone, aliphatic acids such as acetic acid, and mixtures of such water soluble solvents with water, and ethers such as diethyl ether, dimethoxyethane and tetrahydrofuran, or the solvent may be an aromatic or aliphatic hydrocarbon such as benzene, toluene, hexane or cyclohexane. The preferred solvent is toluene. During the reaction, the temperature of the reaction mixture is controlled by cooling, for example, by use of an ice bath. It is preferred that a temperature between −5° C. and 60° C., optimally between 20° C. and 50° C., be maintained during the reaction period. The reaction mixture is stirred for from 1 to 72 hours, preferably for about 24 hours. The reaction may be run in the presence of a base, for example an alkali metal bicarbonate or carbonate such as sodium bicarbonate or potassium carbonate, an alkali metal acetate such as sodium acetate, or an amine such as triethylamine or ethyldiisopropylamine, which reacts with the hydrogen halide liberated in the heterocyclization reaction, resulting in the production of I as a free base. If no base is used, the reaction results in the production of the hydrogen halide salt of I. Following the reaction in the absence of base, the reaction mixture may be quenched into an aqueous solution of a base of the types previously described, neutralizing the hydrogen halide salt.

The neutralized reaction mixture is mixed with a non-water soluble organic solvent, for example, ethyl ether, and the organic layer containing the compound of formula I is separated from the aqueous layer. The organic extract is washed and dried in a conventional manner and the solvent evaporated to guide crude product, which is purified by recrystallization or by silica gel chromatography followed by distillation or crystallization to give the pure N-(alkylphenyl)-4,5-dihydro-2-thiazolamine. Optionally, a pharmaceutically acceptable salt can be prepared by treating the basic product with an appropriate acid, for example hydrochloric, hydrobromic, sulfuric or mathethanesulfonic acid, and recrystallizing the resulting salt.

β-Haloethylisothiocyanates and substituted anilines used as starting materials in the foregoing reaction scheme are commercially available or may be prepared by methods well known in the art. The 3- and 4-alkylanilines may be prepared according to the method of the following Reaction Scheme B:

Reaction Scheme B

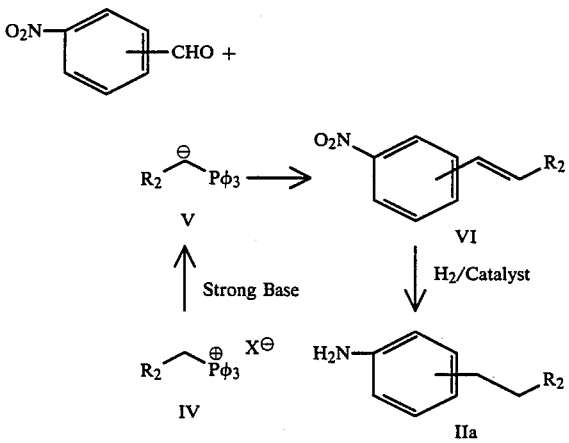

One equivalent of an alkylphosphonium halide salt of formula IV, wherein $R_2$ is a straight chain alkyl group of from 2 to 6 carbon atoms, is dissolved in anhydrous tetrahydrofuran, cooled to about $-10°$ C., treated with a strong base in solution with an organic solvent to generate an ylide of formula V. Suitable bases include alkyl lithium bases such as methyl lithium or butyl lithium, alkali metal amides such as lithium diethyl amide or sodium amide, and alkali metal hydrides such as potassium hydride. Suitable solvents include ethers such as diethyl ether, tetrahydrofuran and dimethoxyethane and hydrocarbons such as hexane, cyclohexane or benzene. This solution is added to a solution of meta- or paranitrobenzaldehyde at a temperature of from $-70°$ to $50°$ C., preferably from $-30°$ C. to $25°$ C., and allowed to react to form a meta- or para-alkenylnitrobenzene of formula VI. The product is isolated and purified by means of standard methods, for example, by extraction followed by distillation, chromatography or crystallization. The purified alkenyl substituted nitrobenzene is then dissolved in an appropriate solvent and reduced catalytically with hydrogen at a pressure between atmospheric pressure and 100 psi, preferably at about 20–50 psi, for from 1 to 10 hours, usually 2 to 3 hours. Preferred catalysts are transition metal catalysts, with 10% palladium on charcoal being most preferred. Appropriate solvents include aqueous or pure ethanol, methanol, ethyl acetate, diethyl ether, tetrahydrofuran, benzene and toluene, ethanol being the preferred solvent. The catalyst is removed by filtration, the solution is concentrated, and the desired alkyl substituted aniline of formula IIa is isolated and purified in the standard way. In formula IIa, the $R_2$ alkyl chain is two carbon atoms shorter than the corresponding R or $R_1$ carbon chain present in formula II. When $R_2$ is a linear akyl chain of from 2 to 6 carbon atoms and para-nitrobenzaldehyde is employed as a starting material, the product of formula IIa is a compound of formula II wherein R is a $C_4$ to $C_6$ alkyl chain and $R_1$ is hydrogen. When $R_2$ is a linear alkyl chain of from 3 to 6 carbon atoms and meta-nitrobenzaldehyde is used as a starting material, the product of formula IIa is a compound of formula II wherein R is hydrogen and $R_1$ is a $C_5$ to $C_8$ alkyl chain.

EXAMPLE 1

N-(4-Hexylphenyl)-4,5-dihydro-2-thiazolamine

A 2 liter, 3-neck round bottom flask fitted with magnetic stirrer, addition funnel, argon gas inlet and thermometer was charged with 4-hexylaniline (65.0 g, 0.367 m) dissolved in 500 ml reagent toluene. To this stirred solution, was added dropwise a solution of β-chloroethylisothiocyanate (53.5 g, 0.441 m, 1.2 eq.) in 175 ml toluene at room temperature. No significant exotherm was noted. After the addition was completed, the reaction mixture was warmed to 50° C. for 19 hours. The reaction was cooled to room temperature and the toluene removed on the rotary evaporator to give an orange, semi-solid residue which was stirred with 900 ml diethyl ether (Et$_2$O). The resulting slurry of off-white solid was cooled in an ice water bath and the solid filtered, washed with cold Et$_2$O, and dried (filter suction, desiccator) to give the slightly impure hydrochloride salt of the desired aminothiazoline. The HCl salt was neutralized by adding the salt to a cold, stirred solution of sodium hydroxide (14.7 g, 0.367 m) in 1200 ml water layered with Et$_2$O. After neutralization, the ether layer was separated and the aqueous layer was extracted with Et$_2$O four times. The combined Et$_2$O extracts were washed with water twice and with a saturated NaCl solution once, dried (MgSO$_4$), and evaporated under vacuum to afford 90.0 g of crude, freebase product as a waxy, off-white solid. The crude material was recrystallized from 900 ml hexane to give 73.0 g (76%) product in two crops as small, off-white platelets. m.p. 77°–79° C.

EXAMPLE 2

3-Hexylaniline

A suspension of butyltriphenylphosphonium bromide (27.3 g, 0.067 m) in 350 ml of dry tetrahydrofuran was cooled to 0° C. under an inert atmosphere of argon. To this stirred suspension was added 0.9 equivalent (0.06 m) of n-butyl lithium in hexane with continued cooling. The mixture was stirred at 0° and as ylide formation proceeded the solid phosphonium salt dissolved with formation of a red-orange solution. After 30 minutes a solution of one equivalent of 3-nitrobenzaldehyde (10.1 g, 0.067 m) in 200 ml of dry tetrahydrofuran was added dropwise to the ylide solution during 30 minutes. The reaction mixture was stirred and allowed to warm to room temperature. After 1 hour the reaction was quenched into 500 ml of saturated ammonium chloride solution and extracted several times with diethyl ether. The combined ether extracts were washed with water and with saturated sodium chloride solution and dried over magnesium sulfate. Filtration of the drying agent and concentration of the ether solution under vacuum afforded a clear brown oil which was purified by silica gel column chromatography to give 3-(1-hexenyl)nitrobenzene (11.0 g, 90% yield) as a clear, light-yellow oil. NMR of this material showed it to be mostly cis configuration at the double bond with some trans isomer present.

The 3-(1-hexenyl)nitrobenzene (11.0 g, 0.054 m) was dissolved in absolute ethanol (500 ml), treated with 1.1 g of 10% palladium on charcoal catalyst and hydrogenated on a Parr apparatus at about 45 psi for 2½ hours. Hydrogen uptake had ceased. The reaction mixture was filtered to remove catalyst, concentrated under vacuum, and then resulting oil purified by Kuglrohr distillation (BP 75°–85° C. at 0.05 mm Hg) to yield 3-hexylaniline (8.6 g, 90% yield) as a clear colorless oil.

EXAMPLE 3

N-(3-Hexylphenyl)-4,5-dihydro-2-thiazolamine

When in the procedure of Example 1, 3-hexylaniline is substituted for 4-hexylaniline, the title compound is obtained. m.p. 79°–80° C.

EXAMPLE 4

N-(4-Butylphenyl)-4,5-dihydro-2-thiazolamine

When in the procedure of Example 1, 4-butylaniline is substituted for 4-hexylaniline, the title compound is obtained. m.p. 73°–75° C.

EXAMPLE 5

N-(4-Pentylphenyl)-4,5-dihydro-2-thiazolamine

When in the procedure of Example 1, 4-pentylaniline is substituted for 4-hexylaniline, the title compounds is obtained. m.p. 77°–78° C.

EXAMPLE 6

N-(4-Heptylphenyl)-4,5-dihydro-2-thiazolamine

When in the procedure of Example 1, 4-heptylaniline is substituted for 4-hexylaniline, the title compound is obtained. m.p. 81°–82° C.

EXAMPLE 7

N-(4-Octylphenyl)-4,5-dihydro-2-thiazolamine

When in the procedure of Example 1, 4-octylaniline is substituted for 4-hexylaniline, the title compound is obtained. m.p. 82°–84° C.

EXAMPLE 8

Cream Formulation for Intravaginal Administration

| Nonaqueous Phase | |
|---|---|
| Cetyl Alcohol | 7.0 g |
| Glycerol monostearate PEG 400 | 8.0 g |
| Diglycol stearate | 6.0 g |
| PEG 400 | 37.5 g |
| N—(4-Hexylphenyl)-4,5-dihydro-2-thiazolamine | 4.0 g |
| Purified water | 37.5 g |
| | 100.0 g |

The nonaqueous phase ingredients were combined and heated with stirring to 60° C. and 4.0 g N-4-hexylphenyl-4,5-dihydro-2-thiazolamine was added and mixed until dissolved. Purified water was heated to 60° C. and added to the nonaqueous phase with agitation. The resulting emulsion was cooled to room temperature with continued agitation.

What is claimed is:

1. A method for the treatment of a fungal infection which comprises topical administration of an effective amount of a compound of formula

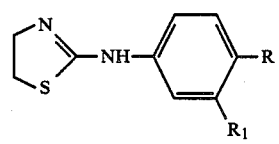

wherein (a) R is a straight chain alkyl group having from 4 to 8 carbon atoms and $R_1$ is hydrogen or (b) R is hydrogen and $R_1$ is a straight chain alkyl group having from 5 to 8 carbon atoms, or a pharmaceutically acceptable salt thereof, in a pharmaceutically acceptable carrier.

2. A method of claim 1 wherein R is a straight chain alkyl group having from 6 to 8 carbon atoms and $R_1$ is H.

3. The method of claim 1 wherein R is N-hexyl and $R_1$ is H.

4. The method of claim 1 wherein the carrier is a cream preparation suitable for vaginal administration.

5. The method of claim 1 wherein the infection being treated as candidiasis.

6. The method of claim 4 wherein the active compound is present as from 2 to 6% of the composition by weight.

7. A composition for topical therapy of a fungal infection in a mammalian host which comprises an effective amount of a compound of the formula

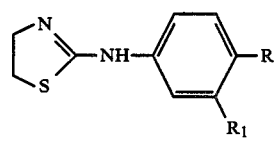

wherein (a) R is a straight chain alkyl group having from 4 to 8 carbon atoms and $R_1$ is hydrogen or (b) R is hydrogen and $R_1$ is a straight chain alkyl group having from 5 to 8 carbon atoms, or a pharmaceutically acceptable salt thereof, in a pharmaceutically acceptable carrier selected from the group consisting of ointments, creams, lotions, gargles, douches, suppositories, tablets, tampons, and patches.

8. A composition of claim 7 wherein R is a straight chain alkyl group having from 6 to 8 carbon atoms and $R_1$ is hydrogen.

9. The composition of claim 7 wherein R is hexyl and $R_1$ is hydrogen.

10. A composition of claim 7 in the form of a cream suitable for vaginal administration.

11. A composition of claim 10 wherein the active compound is present as from 2 to 6% by weight of the composition.

12. A compound of the formula

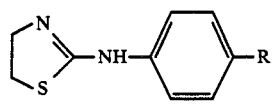

wherein R is a straight chain alkyl group having from 6 to 8 carbon atoms or a pharmaceutically acceptable salt thereof.

13. The compound of claim 12 which is N-(4-hexylphenyl)-4,5-dihydro-2-thiazolamine or a pharmaceutically acceptable salt thereof.

14. The compound of claim 12 which is N-(b 4-heptylphenyl)-4,5-dihydro-2-thiazolamine or a pharmaceutically acceptable salt thereof.

15. The compound of claim 12 which is N-(4-octylphenyl)-4,5-dihydro-2-thiazolamine or a pharmaceutically acceptable salt thereof.

* * * * *